(12) United States Patent
Suzuki et al.

(10) Patent No.: US 6,316,233 B2
(45) Date of Patent: Nov. 13, 2001

(54) PROCESS FOR PREPARING (S)-3-HALOGENO-1,2-PROPANEDIOL BY MICROORGANISM

(75) Inventors: Toshio Suzuki, Osaka; Hideaki Idogaki, Osaka; Atsushi Nakagawa, Osaka; Naoya Kasai, Sennan-gun, all of (JP)

(73) Assignee: Daiso Co., Ltd., Osaka-fu (JP)

( * ) Notice: Subject to any disclaimer, the term of this patent is extended or adjusted under 35 U.S.C. 154(b) by 0 days.

(21) Appl. No.: 09/725,287

(22) Filed: Nov. 29, 2000

(30) Foreign Application Priority Data

Nov. 29, 1999 (JP) .................................................. 11-337812

(51) Int. Cl.⁷ ........................................................ C12P 7/18
(52) U.S. Cl. ........................ 435/158; 435/132; 435/170; 549/513; 549/520
(58) Field of Search ..................................... 435/132, 158, 435/170; 549/513, 520

(56) References Cited

U.S. PATENT DOCUMENTS 5,965,753 * 10/1999 Masaki et al. ........................ 549/513

FOREIGN PATENT DOCUMENTS

| | | |
|---|---|---|
| 0434393 | 6/1991 | (EP) . |
| 0435551 | 7/1991 | (EP) . |
| 0745681 | 12/1996 | (EP) . |
| 62-122596 | 6/1987 | (JP) . |
| 63-36798 | 2/1988 | (JP) . |
| 3-191795 | 8/1991 | (JP) . |
| 6-209781 | 8/1994 | (JP) . |

OTHER PUBLICATIONS

Heathcock, Introduction to Organic Chemistry, Second Addition p. 154, Jan. 1981.*

Database WPI, Section Ch, Week 199435, Derwent Publications Ltd., London, GB; AN 1994–282571, XP002161470.

* cited by examiner

*Primary Examiner*—Leon B. Lankford, Jr.
*Assistant Examiner*—Randall Winston
(74) *Attorney, Agent, or Firm*—Wenderoth, Lind & Ponack, L.L.P.

(57) ABSTRACT

An industrial and economical method for obtaining a (S)-3-halogeno-1,2-propanediol, which comprises cultivating a microorganism belonging to the genus. Pseudomonas which has an ability to assimilate (R)-3-halogeno-1,2-propanediol and can grow by assimilating (R)-3-halogeno-1,2-propanediol as a single carbon source, in a culture medium containing a racemic 3-halogeno-1,2-propanediol as a substrate, and isolating the (S)-3-halogeno-1,2-propanediol from the culture medium.

4 Claims, No Drawings

PROCESS FOR PREPARING (S)-3-HALOGENO-1,2-PROPANEDIOL BY MICROORGANISM

TECHNICAL FIELD

The present invention relates to a process for preparing a (S)-3-halogeno-1,2-propanediol (abbreviated as (S)-[1]) by reacting a racemic 3-halogeno-1,2-propanediol (abbreviated as racemate [1]) with a microorganism which has an ability to grow by assimilating a (R)-3-halogeno-1,2-propanediol (abbreviated as (R)-[1]) as a single carbon source and obtaining (S)-[1].

(S)-3-halogeno-1,2-propanediols are very important as intermediates in making optically active compounds, such as pharmaceuticals, agrochemicals or physiologically active compounds.

PRIOR ART

As to biological or enzymatic methods for preparing a (S)-3-halogeno-1,2-propanediol the following methods are known.

There are two known methods by Takahasi et al. (Japanese Patent Publication A 62-122596, Japanese Patent Publication A 63-36798) and Nikaido et al. (Japanese Patent Application A 6-209781), which comprise reacting racemate [1] with a microorganism to degrade (R)-[1] and recovering remained (S)-[1]. Although, each microorganism used in both methods has an ability to stereoselectively degrade and metabolize (R)-[1] in racemate [1], but the microorganism has not an ability to assimilate (R)-[1] as a single carbon source and therefore, the said microorganism can not grow and propagate in a completely synthetic medium containing racemate [1] as a single carbon source, and an inorganic nitrogen compound such as ammonium sulfate or ammonium nitrate as a nitrogen source. In these methods, in order to obtain (S)-[1] from racemate [1], after the microorganism was separately in a large amount cultivated in a culture medium in which the microorganism can grow, the cells are made to react with racemate [1], or otherwise racemate [1] must be added to a nutrient culture medium in which the microorganism can grow.

Especially, the method of Takahasi et al. belongs to the reaction utilizing the degradatively metabolizing reaction by oxidation, and in order to efficiently progress the reaction, it is necessary to add glutathione or a compound having a SH group such as sodium hydrosulfide or potassium hydrosulfide.

On the other hand, the method of Nikaido et al. is one utilizing a strain belonging to the same genus Pseudomonas as in the present invention, but the strain has not have an ability to assimilate (R)-[1] and therefore, the degradatively assimilating reaction of (R)-[1] with growth of the strain in a synthetic medium containing racemate [1] as a single carbon source does not occur and it is impossible to get (S)-[1].

These two known methods are not convenient and practical from the viewpoints of optical resolution of racemate [1], recovery and purification of (S)-[1] obtained, and are not economical from the viewpoint of the industrial production scale.

DETAILED DESCRIPTION OF INVENTION

The problem to be solved is to provide a method for preparing (S)-[1] from racemate [1] more economically, cheaper and more simply in technique.

The present inventors extensively engaged in seeking a microorganism which has an ability to preferentially assimilate (R)-[1] in racemate [1] and furthermore, can grow by assimilating (R)-[1] as a single carbon source, and have found such a microorganism to complete the present invention.

The present invention relates to a method for obtaining (S)-[1] which comprises cultivating a microorganism belonging to the genus Pseudomonas (abbreviated as the microorganism of the present invention) which has an ability to assimilate (R)-[1] and can grow by assimilating (R)-[1] as a single carbon source, in a culture medium containing racemate [1] as a substrate, and isolating (S)-[1] from the culture medium.

Halogen atoms of racemate [1] used as a substrate in the present invention are preferably chlorine atom and bromine atom.

The present invention is in more detail explained as follows.

The microorganism of the present invention is inoculated into a completely synthetic medium containing racemate [1] as a single carbon source and inorganic compounds such as many kinds of ammonium salts or nitrates as nitrogen sources, and a small amount of metalic salts or inorganic salts such as phosphoric acid salts, and cultivated or reacted to assimilate (R)-[1], and then (S)-[1] remaining in the culture broth is recovered, or the microorganism of the present invention may be cultivated in a nutrient culture medium usually used, such as a bouillon culture medium or a peptone culture medium containing organic carbon sources and nitrogen sources, if necessary inorganic salts, a small amount of metalic salts, or vitamines to assimilate (R)-[1], and then (S)-[1] remaining in the culture broth is recovered.

The present invention, namely relates to the method for recovering (S)-[1] remained in the culture broth or the reaction solution by preferentially degradative assimilating racemate [1] with the microorganism of the present invention.

The assimilating reaction is preferably carried out within optimum pH of the strain used herein and optimum temperature. When the microorganism of the present invention grows by assimilating (R)-[1] as a carbon source, hydrochloric acid in the same amount as (R)-[1] which is degraded with dehalogenation is generated.

When pH gradually becomes lower by hydrochloric acid released from (R)-[1] with progress of the assimilating reaction, it is necessary to adjust pH of the reaction solution to optimum pH by addition of a suitable alkali. For example, the solution is preferably controlled in the range of optimum pH by using a known acid-neutralizing agent, such as an aqueous alkali carbonate solution, e.g. an aqueous calcium carbonate solution, an aqueous sodium carbonate solution, an aqueous potassium carbonate solution or an aqueous ammonium carbonate solution, an aqueous alkali hydroxide solution, e.g. sodium hydroxide solution, an aqueous potassium hydroxide solution or an aqueous calcium hydroxide solution, or an aqueous ammonium solution.

The culture medium for cultivation of the microorganism of the present invention and for making assimilating reaction of (R)-[1] is preferably a completely synthetic medium containing racemate [1] as a single carbon source, inorganic compounds such as many kinds of ammonium salts or nitric acid salts as nitrogen sources, and a small amount of metalic salts, or inorganic salts such as a phosphoric acid salt in the economical viewpoint, but is not limited as long as the conventional culture medium containing racemate [1] as a substrate in which the microorganism of the present invention can grow. For example, carbohydrates such as glucose or fructose, alcohols such as glycerol, sorbitol, or mannitol, organic acids, such as acetic acid, citric acid, malic acid, maleic acid, fumaric acid or gluconic acid, or a salt thereof, or a mixture thereof, can be used as carbon source.

Inorganic nitrogen compounds such as ammonium sulfate, ammonium nitrate or ammonium phosphate, organic nitrogen compounds such as urea, peptone, casein, yeast extract, meat extract, corn steep liquor or a mixture thereof, can be used as nitrogen source. Furthermore, inorganic salts such as a phosphoric acid salt, metalic salts such as a magnesium salt, a potassium salt, a manganese salt, an iron salt, a zinc salt, or a copper salt, or if suitable, vitamins may be used.

The cultivation mentioned above is aerobically carried out in an usual manner, at pH 4–10, preferably 5–9, at 15–50° C., preferably 20–37° C. under stirring or agitating for 20–96 hours.

The microorganism of the present invention may be previously cultivated in a nutrient culture medium usually used, such as a bouillon culture medium or a peptone culture medium containing organic carbon sources and nitrogen sources, and if necessary inorganic salts, a small amount of metalic salts, or vitamines.

As enzyme-inducing additives to obtain the microorganism having high enzyme activity, to the above mentioned culture medium, or a nutrient culture medium such as a peptone culture medium or a bouillon culture medium may be added a 3-halogeno-1,2-propanediol such as racemic 3-chloro-1,2-propanediol or racemic 3-bromo-1,2-propanediol.

The concentration of the substrate in the reaction mixture is preferably 0.1–15% (v/v) and the substrate may be added at once in the initial stage or in several times.

The reaction is aerobically carried out under shaking or agitation according to the usual method, and the reaction is preferably completed in 24–120 hours, depending on the concentration of the substrate or other reaction conditions. When the residual amount of the substrate (racemate [1]) becomes 50% comparing with the initial concentration of the substrate by gas chromatography, the reaction is preferably finished, or with measurement of optical purity on the optically active object-compound ((S)-[1]), the end point may be preferably determined. That is, it is preferable to quench the reaction at the time when (R)-[1] in racemate [1] is completely assimilated.

Thus obtained (S)-[1] remaining in the reaction solution is recovered, separated and purified by the conventional method. For example, after removal of the cells from the reaction medium by centrifugation, the supernatant is condensed with an evaporator, extracted with a solvent such as ethyl acetate, ethanol, etc. The extract is dried over anhydrous magnesium sulfate, and then the solvent is evaporated in vacuo to obtain (S)-[1] in syrup. Additionally, the purification by distillation may be carried out.

The microorganism of the present invention is one belonging to the genus Pseudomonas, illustratively Pseudomonas sp. DS-SI-5. This strain was identified to a strain belonging to species of the genus Pseudomonas from its physiological and bacteriological properties and already deposited with the National Institute of Bioscience and Human-Technology Agency of Industrial Science and Technology, Japan under Budapest Treaty with an accession number of FERM BP-7080.

The present invention is illustratively explained by following examples, but should not be limited by these examples. Percentage (%) in examples means % (w/v), if not defined otherwise.

EXAMPLE 1

A culture medium (100 ml, pH 6.9) consisting of

| Ammonium sulfate | 0.5% |
|---|---|
| Sodium monohydrogen phosphate | 0.02% |
| Potassium monohydrogen phosphate | 0.02% |
| Sodium dihydrogen phosphate | 0.04% |
| Magnesium sulfate | 0.05% |
| Copper sulfate | 0.0001% |
| Manganese nitrate | 0.0001% and |
| Calcium carbonate | 0.45% | were poured into a 500 ml Erlenmeyer flask with baffles and the flask was sterilized at 121° C. for 15 minutes by autoclaving. Thereto racemic 3-chloro-1,2-propanediol (1 ml, 1.3 g) was added to prepare a completely synthetic medium containing racemic 3-chloro-1,2-propanediol as a single carbon source. And then, Pseudomonas sp. DS-SI-5 was previously incubated in a gradient agar culture medium containing polypeptone (1.0%), yeast extract (1.0%) and D-glucose (1.0%) and a loopful of the strain was aseptically inoculated into the above synthetic medium. The culture medium was cultivated with rotary shaking (130 rpm) at 30° C. for 2 days. At that time the remaining amount of racemic 3-chloro-1,2-propanediol was measured with gas chromatography (GL Science Co., Ltd. column support: PEG20M, 60–80 mesh, 0.31–0.42mm) to be 45% in the remaining ratio. After the cultivation being over, the culture broth was taken out, and the cells were removed by centrifugation to give a supernatant. The supernatant was concentrated to about 2 ml by evaporator and extracted with ethyl acetate. The extract was dried over magnesium sulfate and the solvent was removed in vacuo to give 0.51 g of 3-chloro-1,2-propanediol as a syrup.

The measurement of optical purity of the product thus obtained was carried out by subjecting the product to gas chromatography with Capillary column: astec CHIRAL-DEX G-TA (inner diameter; 0.25 mm×30 m) after the conversion of the product (an optical isomer of 3-chloro-1,2-propanediol) into the corresponding optical isomer of glycidol by alkali-treating with an aqueous sodium hydroxide solution [Suzuki et al., Appln. Microbiol. Biotechnol., Vol.40,273–278(1993)].

As a result, 3-chloro-1,2-propanediol obtained was 99% ee in the optical purity and was (S)-form.

Conditions on the above gas chromatography analysis were as follows:

Retention time of glycidol: (R)-form, 80.6 min.; (S)-form, 82.1 min.

Analysis temperature: Column temp. (45° C.), Inject temp. 200° C.

Carrier gas: nitrogen (flow 0.5 ml/min.), Split ratio:200/1, Detection: FID 200° C.

EXAMPLE 2

A nutrient culture medium (100 ml, pH 7.2) consisting of polypeptone (1.0%), yeast extract (1.0%) and D-glucose (1.0%) were poured into a 500 ml Erlenmeyer flask with baffles and the flask was sterilized under vapor pressure at 121° C. for 15 minutes to prepare a liquid nutrient culture medium. A loopful of Pseudomonas sp. DS-SI-5 which was previously cultivated in a gradient agar nutrient culture medium of the above ingredients was inoculated into the above liquid medium. The culture medium was cultivated with rotary shaking (130 rpm) at 30° C. for 24 hours. The cells were harvested by centrifugation and washed twice by phosphate buffer (50 m M, pH 7.2) to prepare washed cells. The cells were suspended in the culture medium (101 ml) containing racemic 3-chloro-1,2-propanediol as a single carbon source shown in Example 1 and were reacted by agitation (130 rpm) at 30° C. for 2 days. The remaining amount of racemic 3-chloro-1,2-propanediol was measured in a same manner as in Example 1 to be 46% in the remaining ratio. After the reaction, the cells were removed by centrifugation to give a supernatant. The recovery of 3-chloro-1,2-propanediol from the supernatant was conducted in the same method as in Example 1 to obtain 0.52 g of the product.

As a result of measurement on optical purity of the product in the same method as in Example 1, 3-chloro-1,2-propanediol obtained was 99% ee in the optical purity and was (S)-form.

EXAMPLE 3

A culture medium (2.5 L, pH 6.9) consisting of

| | |
|---|---|
| Ammonium sulfate | 0.5% |
| Sodium monohydrogen phosphate | 0.02% |
| Potassium monohydrogen phosphate | 0.02% |
| Sodium dihydrogen phosphate | 0.04% |
| Magnesium sulfate | 0.05% |
| Ferric sulfate | 0.001% |
| Copper sulfate | 0.0001% and |
| Manganese nitrate | 0.0001% | were put into a 5 L fermenter (jar fermenter, Mitsuwa Rikagaku Co., Ltd. Model KMJ5 B) and sterilized under vapor pressure at 121° C. for 15 minutes. Thereto racemic 3-chloro-1,2-propanediol (25 ml, 32.5 g) was added to prepare a completely synthetic medium containing racemic 3-chloro-1,2-propanediol as a single carbon source. And then, Pseudomonas sp. DS-SI-5 was previously incubated under shaking in a nutrient culture medium containing polypeptone (1.0%), yeast extract (1.0%) and D-glucose (1.0%) at 30° C. for 24 hours, and 50 ml [2%(v/v)] of the culture broth were aseptically inoculated into the above synthetic medium. The culture medium was aerobically (airation: 0.5 L/min) cultivated with agitation (500 rpm) at 30° C. for 3 days.

Measurement of pH and its control was conducted with a pH controller and pH was adjusted to 6.9 with an aqueous sodium hydroxide solution (3 mmol/L).

The measurement and identification of the product was conducted in the same method as in Example 1.

After the cultivation being over, the culture broth was taken out, and the cells were removed by centrifugation to give a supernatant. The recovery of 3-chloro-1,2-propanediol was conducted in the same method as in Example 1 to give 13.7 g of the product. As a result of measurement on optical purity of the product in the same method as in Example 1, 3-chloro-1,2-propanediol obtained was 99% ee in the optical purity and was (S)-form.

EXAMPLES 4–6

Experiments (three kinds) were conducted according to the procedures of the above Examples 1–3, except for using racemic 3-bromo-1,2-propanediol as a substrate instead of racemic 3-chloro-1,2-propanediol.

As results, optically purity and optical isomer of 3-bromo-1,2-propanediol obtained were 96% ee and (S)-form, respectively. The remaining amount of 3-bromo-1,2-propanediol was 0.24 g, 0.28 g and 6.2 g, respectively.

EFFECT OF INVENTION

According to the present invention, by cultivating a microorganism belonging to the genus Pseudomonas, especially Pseudomonas sp. DS-SI-5 having an ability to assimilate (R)-[1] in the culture medium containing racemate [1] as a substrate, especially in the culture medium containing the racemate as a single carbon source, and by preferentially degradative assimilating (R)-[1] to obtain (S)-[1] economically and in industrial simple.

On the other hand, according to the present invention, even if (S)-[1] is prepared in industrial scale, it is not necessary to prepare a large amount of cells by cultivation the strain separately and it is enough to cultivate the amount of the strain useful as starter and inoculate it, namely it is enough if only one microorganism is there.

What is claimed is:

1. A method for obtaining a (S)-3-halogeno-1,2-propanediol, which comprises cultivating Pseudomonas sp. DS-SI-5 (FERM-7050) in a culture medium containing a racemic 3-halogeno-1,2-propanediol as a substrate, and isolating the (S)-3-halogeno-1,2-propanediol from the culture medium.

2. The method of claim 1, which comprises cultivating the Pseudomonas sp, in the culture medium containing a racemic 3-halogeno-1,2-propanediol as a single carbon source.

3. The method of claim 2 for obtaining a (S)-3-chloro-1,2 propanediol or (S)-3-bromo-1,2-propanediol, which comprises using a racemic 3-chloro-1,2 propanediol or racemic 3-bromo-1,2-propanediol as a substrate.

4. The method of claim 1 for obtaining a (S)-3-chloro-1,2 propanediol or (S)-3-bromo-1,2-propanediol, which comprises using a racemic 3-chloro-1,2 propanediol or racemic 3-bromo-1,2-propanediol as a substrate.

* * * * *